United States Patent
Liao et al.

(10) Patent No.: US 10,814,305 B2
(45) Date of Patent: Oct. 27, 2020

(54) AGAROSE-FILLED CERAMIC APATITE

(71) Applicant: BIO-RAD LABORATORIES, INC., Hercules, CA (US)

(72) Inventors: Jiali Liao, Hercules, CA (US); Christopher Belisle, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 327 days.

(21) Appl. No.: 15/714,368

(22) Filed: Sep. 25, 2017

(65) Prior Publication Data

US 2018/0085735 A1     Mar. 29, 2018

Related U.S. Application Data

(60) Provisional application No. 62/401,560, filed on Sep. 29, 2016.

(51) Int. Cl.

| | |
|---|---|
| *B01D 15/38* | (2006.01) |
| *B01J 20/04* | (2006.01) |
| *B01J 20/24* | (2006.01) |
| *B01J 20/28* | (2006.01) |
| *B01J 20/285* | (2006.01) |
| *C07K 1/16* | (2006.01) |
| *C07K 1/18* | (2006.01) |

(Continued)

(52) U.S. Cl.
CPC .......... *B01J 20/24* (2013.01); *B01D 15/3809* (2013.01); *B01J 20/048* (2013.01); *B01J 20/285* (2013.01); *B01J 20/28016* (2013.01); *C07K 1/165* (2013.01); *C07K 1/18* (2013.01); *C07K 1/22* (2013.01); *C07K 1/36* (2013.01); *C07K 14/435* (2013.01); *C07K 16/00* (2013.01); *C07K 16/065* (2013.01); *B01D 15/3847* (2013.01); *B01J 2220/80* (2013.01)

(58) Field of Classification Search
CPC .... B01J 20/24; B01J 20/048; B01J 20/28016; B01J 20/285; B01J 2220/80; B01D 15/2809; B01D 15/3809; B01D 15/3847; C07K 1/22; C07K 1/36; C07K 14/435; C07K 16/00; C07K 1/165; C07K 1/18; C07K 16/065

See application file for complete search history.

(56) References Cited

U.S. PATENT DOCUMENTS

| | | | |
|---|---|---|---|
| 4,971,833 A | 11/1990 | Larsson et al. | |
| 6,368,703 B1 * | 4/2002 | Johnson | B32B 5/18 |
| | | | 428/218 |

(Continued)

FOREIGN PATENT DOCUMENTS

| | | |
|---|---|---|
| BR | PI0702934 A2 | 2/2009 |
| CN | 103923355 A | 7/2014 |

(Continued)

OTHER PUBLICATIONS

Bio-Rad Laboratories, "CHT Ceramic Hydroxyapatite", Bulletin 5667 Rev B. July. (Year: 2013).*

(Continued)

*Primary Examiner* — Benjamin L Lebron
(74) *Attorney, Agent, or Firm* — Kilpatrick Townsend and Stockton LLP

(57) ABSTRACT

Polymer-filled ceramic apatites and their uses are provided.

20 Claims, 1 Drawing Sheet

(51) Int. Cl.
*C07K 1/22* (2006.01)
*C07K 1/36* (2006.01)
*C07K 14/435* (2006.01)
*C07K 16/00* (2006.01)
*C07K 16/06* (2006.01)

(56) References Cited

U.S. PATENT DOCUMENTS

| | | | |
|---|---|---|---|
| 6,423,666 | B1 | 7/2002 | Liao et al. |
| 6,972,090 | B2 | 12/2005 | Boschetti et al. |
| 8,093,373 | B2 | 1/2012 | Alstine et al. |
| 8,182,831 | B2 | 5/2012 | Lin et al. |
| 8,574,437 | B2 | 11/2013 | Bergstrom et al. |
| 8,814,936 | B2 | 8/2014 | Draenert |
| 9,155,980 | B2 | 10/2015 | Glad et al. |
| 9,259,729 | B2 | 2/2016 | Bergstrom et al. |
| 9,278,297 | B2 | 3/2016 | Bergstrom et al. |
| 9,382,473 | B2 * | 7/2016 | Chiu .................. B82Y 30/00 |
| 9,383,299 | B2 | 7/2016 | Kunkel et al. |
| 2003/0125529 | A1 | 7/2003 | Boschetti et al. |
| 2003/0166869 | A1 * | 9/2003 | Vedantham ............ C07K 1/16 530/387.1 |
| 2006/0246524 | A1 * | 11/2006 | Bauer ................ A61K 49/0058 435/7.92 |
| 2007/0072303 | A1 * | 3/2007 | Arpaia .................... C07K 1/16 436/86 |
| 2011/0045574 | A1 | 2/2011 | Bergstrom et al. |
| 2012/0141497 | A1 * | 6/2012 | Gallo .................... C07K 1/18 424/158.1 |
| 2013/0034854 | A1 * | 2/2013 | Ashworth-Sharpe ..... C07F 9/12 435/6.11 |

FOREIGN PATENT DOCUMENTS

| | | |
|---|---|---|
| EP | 1 131 383 B1 | 10/2003 |
| EP | 1 071 500 B1 | 3/2005 |
| GB | 2324601 A | 10/1998 |
| WO | 2007/008250 A2 | 1/2007 |
| WO | 2010/051360 A1 | 5/2010 |
| WO | 2013/096831 A1 | 6/2013 |
| WO | WO 2015/137860 A1 | 9/2015 |

OTHER PUBLICATIONS

Machine Translation of Wang (CN 10392335).*
Fisher Scientific, "Centrifugation Theory". Accessed Jun. 16, 2020.*
"BioSepra HA Ultrogel: Process Proteomics Product Note" (Oct. 2002), BioSepra S.A., Ciphergen BioSepra Process Division, pp. 1-4.
"Purification of influenza A/H1N1 using Capto Core 700," Data file: 29-0003-34 AA, GE Healthcare Bio-Sciences AB, (Mar. 2012), pp. 1-8.
Zhang, Yue et al., "Light-induced Crosslinkable Semiconducting Polymer Dots," NIH Public Access, Chemical Science, (Mar. 2015), vol. 6(3), pp. 2102-2109.
"Capto Core 700", GE Healthcare Life Sciences, Data file: 28-9983-07 AA, Multimodal chromatography, Mar. 2012, pp. 1-4.
BioSepra HA Ultrogel, product Insert, Insert No.: 292200, PALL Life Sciences, (Mar. 2007) 2 pp.
Pall Life Sciences, "BioSepra HA Ultrogel: Product Note", [available online at https:/lshop.pall.com/INTERSHOP/web/WFS/PALL-PALLUS-Site/en_US/-/USDNiewProductAttachment-OpenFile?LocaleId=&DirectoryPath=pdfs%2FBiopharmaceuticals&FileName=HA_Uitrogei_Pall, Aug. 29, 2006.
Kolanthai, et al., "Synthesis of nanosized hydroxyapatite/agarose powders for bone filler and drug delivery application", Materials Today Communications, vol. 8, May 16, 2016, pp. 31-40.
PCT/US2017/053217, "International Search Report and Written Opinion", Dec. 11, 2017, 9 pages.
Extended European Search Report in EP Appln. 17857257.4 dated Apr. 2, 2020; 13 pages.

* cited by examiner

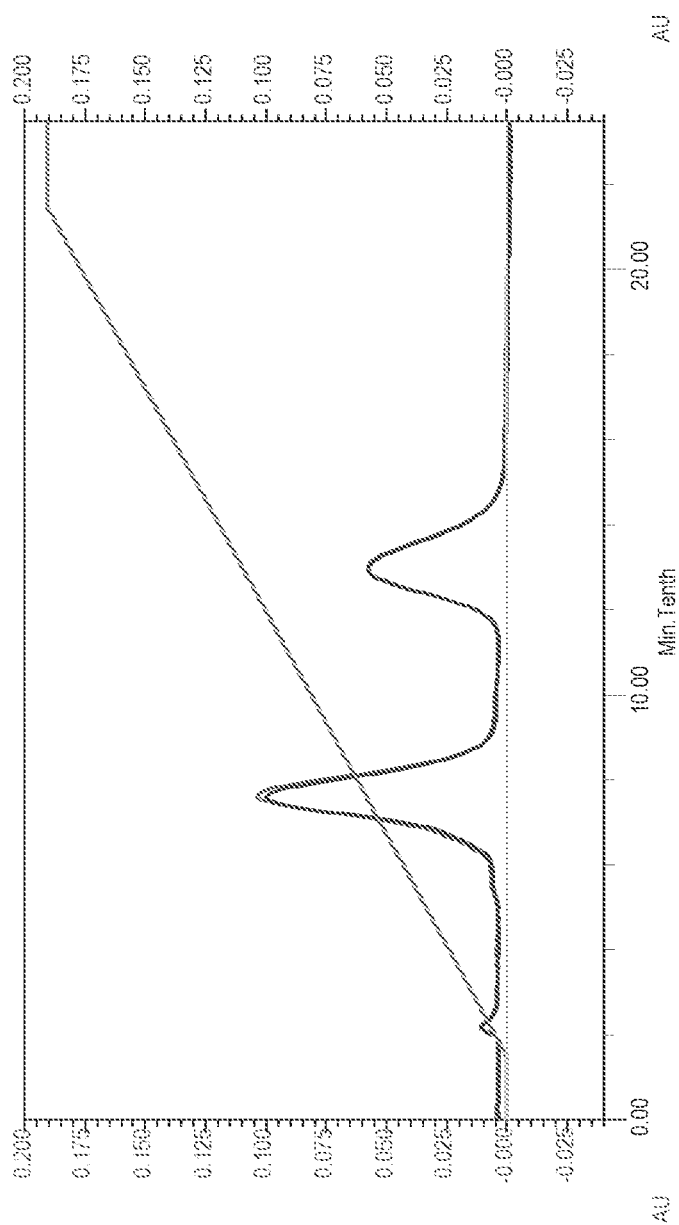

AGAROSE-FILLED CERAMIC APATITE

This application claims the benefit of U.S. Provisional Application 62/401,560 filed on Sep. 29, 2016 which is hereby incorporated by reference in its entirety.

BACKGROUND OF THE INVENTION

Purification of viruses, proteins conjugated to large particles, and other large biomolecules from smaller impurities currently involves using a variety of separation methods including, but not limited to, size exclusion chromatography (SEC), ion exchange chromatography (IEX), hydrophobic interaction chromatography (HIC) and/or centrifugation. SEC requires large columns packed with expensive size exclusion resin, low flow rates and limited sample loads. IEX and HIC have limited selectivity. Centrifugation can only be applied to large biomolecules that are relatively dense compared to the medium in which the biomolecules are suspended.

BRIEF SUMMARY OF THE INVENTION

Provided herein is a ceramic apatite bead comprising an insoluble porous polymer. In some embodiments, the polymer is agarose. In some embodiments, the agarose is not cross-linked. In some embodiments, the agarose has a concentration ranging from about 1 to about 8%.

In some embodiments, the ceramic apatite is ceramic hydroxyapatite.

Also provided is a chromatography column comprising a plurality of ceramic apatite beads containing an insoluble porous polymer, e.g., as described above or elsewhere herein.

Also provided is a method of preparing the ceramic apatite bead containing an insoluble porous polymer, e.g., as described above or elsewhere herein. In some embodiments, the method comprises incubating ceramic apatite in a heated polymer solution; and cooling the heated polymer solution having ceramic apatite to between about 4° C. to about 30° C.) to form an insoluble porous polymer gel within the pores of the ceramic apatite. In certain embodiments, the incubating step causes the polymer to absorb or otherwise enter into pores of the ceramic apatite. In some embodiments, a temperature of the heated polymer solution is about 100° C. In certain embodiments, the heated polymer solution comprises a sufficient concentration of polymer to further coat an outer surface of the ceramic apatite. In some embodiments, the polymer is agarose and the concentration of the agarose is more than about 1%, 2%, 3%, or 4%. In some embodiments, the concentration of the agarose is about 4%. In some embodiments, excess polymer is removed prior to the cooling step. In certain embodiments, the incubating step comprises adding a heated organic solvent and a nonionic detergent to the heated polymer solution while stirring. In some embodiments, the organic solvent is at least partially immiscible with water and is chemically inert relative to the polymer in the heated polymer solution. In some embodiments, the organic solvent is an isoparaffin (e.g., Isopar H). In some embodiments, the temperature of the heated organic solvent is from about 60° C. to about 80° C. In some embodiments, the nonionic detergent is selected from the group consisting of a sorbitan derivative, an ethoxylated alkylphenol, and a polyethoxylated ester. In some embodiments, the sorbitan derivative is a sorbitan ester (e.g., Span 80) or a polyethoxylated sorbitan ester.

Also provided are methods of performing chromatography. In some embodiments, the method comprises contacting a sample comprising a target molecule to a plurality of ceramic apatite beads comprising an insoluble porous polymer, e.g., as described herein, under conditions such that the target is not captured by the ceramic apatite beads; and collecting the target molecule from the ceramic apatite beads. In some embodiments, the sample comprises a contaminant that is captured by the ceramic apatite beads. In some embodiments, the target molecule is a protein-nanoparticle conjugate and the contaminant is free (unconjugated) protein. In some embodiments, the sample comprises the protein-nanoparticle conjugate, free protein, and a buffer. In some embodiments, the sample further comprises a surfactant (e.g., polyalkylene glycol or Pluronic F-68). In certain embodiments, the collecting step comprises collecting one or more fractions enriched for the target molecule from the ceramic apatite beads. In some embodiments, the collecting step comprises applying centrifugal force or a vacuum to the ceramic apatite beads and collecting one or more fractions enriched for the target molecule from the ceramic apatite beads. In some embodiments, the protein is an antibody. In some embodiments, the protein is an IgG antibody. In certain embodiments, the protein-nanoparticle conjugate is a protein-polymer dot conjugate. In some embodiments, the sample further comprises free nanoparticles and the ceramic apatite beads separate the free nanoparticles from the conjugate.

BRIEF DESCRIPTION OF THE DRAWINGS

FIG. 1 is an overlay chromatogram showing the similar selectivity of standard ceramic hydroxyapatite (CHT) and agarose-filed CHT.

DETAILED DESCRIPTION OF THE INVENTION

The inventors have discovered a novel polymer-filled ceramic apatite having multimodal properties, i.e., a size exclusion mode and a capture mode. The inventors have also discovered that insoluble porous polymers can be introduced into ceramic apatites without significantly affecting the ceramic apatite selectivity or binding capacity.

Definitions

The term "hydroxyapatite" refers to an insoluble hydroxylated mineral of calcium phosphate with the structural formula $Ca_{10}(PO_4)_6(OH)_2$. Hydroxyapatite chromatography resin is considered a multimodal resin in that it has multiple modes of interaction with biomolecules. Its dominant modes of interaction are phosphoryl cation exchange and calcium metal affinity. Hydroxapatite is commercially available in a variety of forms including, but not limited to, ceramic hydroxyapatite which is a chemically pure form of hydroxyapatite that has been sintered at high temperature to modify it from a crystalline to a ceramic form. Ceramic hydroxyapatite is spherical in shape, with particle diameters ranging from about 10 microns to about 100 microns, and is typically available at nominal diameters of 20 microns, 40 microns, and 80 microns. Ceramic hydroxyapatite (or CHT) is macroporous, and is available in two types: Type I, with a medium porosity and a relatively high binding capacity, and Type II, with a larger porosity and a lower binding capacity. All of the apatite-based resins in this paragraph are available from Bio-Rad Laboratories, Inc. (Hercules, Calif., USA).

The term "antibody" refers to an immunoglobulin or fragmentary form thereof. The term includes, but is not limited to, polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" encompasses composite forms including, but not limited to, fusion proteins containing an immunoglobulin moiety. "Antibody" also includes antibody fragments such as Fab, F(ab')2, Fv, scFv, Fd, dAb, Fc and other compositions, whether or not they retain antigen-binding function.

The term "protein" is used to denote an amino acid polymer or a set of two or more interacting or bound amino acid polymers. The term applies to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "sample" refers to any composition containing a target molecule that is desired to be purified. In some embodiments, the target molecule to be purified is a protein-nanoparticle conjugate (e.g., an antibody-nanoparticle conjugate) or a virus.

The term "contaminant" refers to any impurity that is to be removed from a sample. In some embodiments, the sample is a conjugation reaction mixture of antibody-nanoparticle conjugate and unreacted components and the contaminant is unconjugated (unreacted or free) antibody (and optionally unconjugated nanoparticles).

As used herein, the terms "a", "an" and "the" are intended to mean "one or more." As used herein, the term "about" refers to the recited number and any value within 10% of the recited number. Thus, "about 5" refers to any value between 4.5 and 5.5, including 4.5 and 5.5.

Polymer-Filled Ceramic Apatite

A variety of polymers can be used to fill the ceramic apatite. In an embodiment, the polymer is insoluble such that the aqueous conditions of chromatography do not remove the polymer from the ceramic apatite during chromatography. In embodiments, the polymer is sufficiently porous so that filling the ceramic apatite does not prevent macromolecules (e.g., proteins, nucleic acids, etc.) from interacting with sites within the ceramic apatite, thereby substantially maintaining the selectivity and binding capacity of the ceramic apatite. Ceramic apatite is porous and allows target molecules to interact with ceramic apatite, at least in part, via pores in the apatite. Thus, the polymer should not significantly interfere with this interaction.

In some embodiments, the polymer is agarose. Agarose (e.g., 1-8%) can be introduced into the ceramic apatite by heating the agarose to a uniform density and mixing the heated agarose solution with ceramic apatite. In some embodiments, the agarose solution is heated to about 100° C. In certain embodiments, the agarose solution is heated from about 60° C. to about 100° C.

In some embodiments, a heated organic solvent and a nonionic detergent are added to the heated polymer solution while stirring to create a stable suspension and to prevent the pore-filled ceramic apatite particles from aggregating. In some embodiments, the organic solvent is relatively immiscible with water and is chemically inert relative to the polymer in the heated polymer solution. In certain embodiments, the organic solvent is an isoparaffin (e.g., Isopar C, Isopar E, Isopar G, Isopar H, Isopar K, Isopar L, Isopar M, and/or Isopar V). In some embodiments, the nonionic detergent is a sorbitan derivative, an ethoxylated alkylphenol, and/or a polyethoxylated ester. In certain embodiments, the sorbitan derivative is a sorbitan ester (e.g., Span 20, Span 40, Span 60, Span 80, Span 83, Span 85, and/or Span 120) and/or a polyethoxylated sorbitan ester (e.g., Tween 20, Tween 40, Tween 60, Tween 65, and/or Tween 80).

In some embodiments, the agarose in the heated agarose solution is at a sufficient concentration (e.g., more than about 1%, 2%, 3%, or 4% agarose) to fill the pores of the ceramic apatite and to coat the outside of the ceramic apatite. Excess agarose solution can subsequently be removed by filtering with positive or negative (e.g., vacuum) pressure. The agarose solution inside the beads forms an insoluble gel at temperature less than about 40° C.

In some embodiments, the agarose will not be cross-linked. For instance, as described in the examples, the agarose is introduced into the ceramic apatite in uncross-linked form. However, in some embodiments, a cross-linking agent is introduced after the agarose has filled the ceramic apatite. Thus, in some embodiments, the agarose within the ceramic apatite will be cross-linked.

Generally, the agarose will not be functionalized. Thus, in some embodiments, the agarose will not be modified to interact with components of the sample during chromatography, thereby providing substantially the same selectivity as the ceramic apatite without the polymer. In other embodiments, the agarose will be functionalized. For example, the agarose can be functionalized with, for example, mixed-mode ligands, ion exchange ligands, and/or affinity functional groups.

A variety of apatites suitable for chromatography can be used in the methods and compositions described herein. In some embodiments, Type 1 or Type II ceramic apatite can be used (i.e., either porosity can be used). The optimal porosity for any particular protein separation or purification will vary with the proteins or the composition of the source mixture.

The polymer-filled ceramic apatite can be used as a chromatographic solid phase in the form of a packed bed, and can constitute either the entire packed bed or a major portion, such as 50% or more by volume, of the packed bed. The packed bed can be retained in a vessel of any configuration, and both the purification performed in the resin and the cleaning and regeneration can be performed either as a batch process, a continuous process, or a hybrid batch/continuous process. In an embodiment, the vessel is a column having an appropriate length relative to width and a suitable process includes a continuous process such as a continuous flow through a column.

The beads have a size exclusion mode and a capture mode. The size exclusion mode separates molecules, complexes or particles based on their size or molecular weight. The beads have pores sized such that molecules, complexes or particles above a size threshold are excluded from entering the pores and are collected in a void volume, an excluded volume or in a chromatography column flow through. Smaller proteins and other molecules can enter the pores of the beads and are captured by the beads. As used herein, a molecular weight cutoff size of the beads refers to the approximate size of the protein or molecule that is able to enter the pores. For example, a molecular weight cutoff size (or size exclusion limit) of 50000 Daltons (or 50 kDa) means that molecules of approximately 50 kDa or less in size can enter the pores of the medium, whereas molecules of approximately more than 50 kDa will be excluded from the pores. As the percent of agarose filling the pores of the ceramic apatite beads increases, the pores become smaller, resulting in a lower molecular weight cutoff size. Thus, the molecular weight cutoff for 4% agarose-filled beads will be less than the molecular weight cutoff for 1% agarose-filled beads.

Methods

The polymer-filled ceramic apatites as described herein can be used in a chromatography method. In an embodiment, the method comprises contacting a sample comprising a target molecule to a plurality of agarose-filled ceramic apatite beads as described herein under conditions such that the target is not captured by the beads. In an embodiment, the sample comprises a contaminant that is captured by the ceramic apatite beads.

Before the sample is applied to the polymer-filled ceramic apatite, the apatite-based resin is often equilibrated in the buffer or salt used to load the sample. Generally, the same conditions and reagents are used as in standard ceramic apatite-based chromatography. Any of a variety of buffers or salts can be used, including those with cations such as sodium, potassium, ammonium, magnesium, and calcium, and anions such as chloride, fluoride, acetate, phosphate, and citrate. The pH of the equilibration solution is typically about 6.0 or higher, in many cases the pH is within the range of about 6.5 to about 8.6 or a range of about 6.5 to about 7.8. In some embodiments, equilibration may take place in a solution comprising a Tris or a sodium phosphate buffer. The sodium phosphate buffer may be, for example, present at a concentration from about 0.5 mM to about 50 mM, or from about 10 mM to about 35 mM.

As noted above, the chromatographic step described herein can be performed in a conventional purification configuration including, but not limited to, packed columns and fluidized or expanded-bed columns and by any conventional chromatography method including batch modes for loading, washing, and elution, as well as continuous or flow-through modes. In some embodiments, the medium is packed in a column having a diameter ranging from less than 0.5 centimeter to more than a meter and a column height ranging from less than one centimeter to more than 30 centimeters. In an embodiment, the resin is provided in a spin column. The sample is applied to the top of the spin column and centrifugation or vacuum forces the sample through the column. In some cases, the resin is provided in a chromatography column, the sample is applied to the top of the column and gravity forces the sample through the column. The column can be run with or without pressure and from top to bottom or bottom to top, and the direction of the flow of fluid in the column can be reversed during the process. In some cases, it can be advantageous to reverse the flow of liquid while maintaining the packed configuration of the packed bed.

The method described herein can be used for purifying many types of target molecules (e.g., large target molecules), including viruses, naturally occurring proteins, and recombinant proteins. In some embodiments, the target molecule is conjugated or attached to a reporter, e.g., a nanoparticle. In some embodiments, the target molecule is an antibody (e.g., IgG) conjugated to a nanoparticle. Nanoparticles are particles sized on a nanoscale, e.g., from about 1 nm to about 1000 nm. In some embodiments, the particles are between 1-300 nm, 5-500 nm, or 10-50 nm. Many nanoparticles are roughly spherical in shape, which results in a dimension being the radius or diameter of the spherical particle. The hydrodynamic radius or diameter can also be used to define the nanoparticle size.

In some embodiments, the nanoparticle is a fluorescent semiconducting polymer dot (pdot). Examples of such pdots are described in, e.g., Wu, C., et al., *Chem. Mater.* 21:3816-3822 (2009); Rahim, N. A. A., et al., *Adv. Mater.* 21:3492-3496 (2009), Rong et al., *ACS Nano* 7(1):376-84 (2013); patent publications U.S. 2013/0266957; WO 2012/054525; and U.S. 2012/0282632. Chromophoric pdots can be generated by collapsing polymers into a stable sub-micron sized particle. The pdot nanoparticles provided herein may be formed by any method known in the art for collapsing polymers, including without limitation, methods relying on precipitation, methods relying on the formation of emulsions (e.g. mini or micro emulsion), and methods relying on condensation. The pdot nanoparticle size is dependent on the molecular weight of the polymer used to generate the pdots (see, for example, Zhang, Y., et al., *Chem Sci.* 6(3):2102-2109 (2015) and U.S. Pat. No. 9,382,473). In some embodiments, the molecular weight of each pdot ranges from about 500,000 Daltons to about 15,000,000 Daltons, or from about 1,800,000 Daltons to about 7,000,000 Daltons.

Other exemplary nanoparticles that can be used in methods described herein include, but are not limited to, magnetic nanoparticles, quantum dots, and gold nanoparticles. Magnetic nanoparticles are a class of nanoparticle that can be manipulated using magnetic field gradients. Magnetic nanoparticles are formed from magnetic or paramagnetic elements including, but not limited to, iron, nickel and cobalt and their chemical compounds. Quantum dots are nanoparticles formed from inorganic semiconducting material. Gold nanoparticles (e.g., colloidal gold) have optical properties that are conducive to biomedical applications and are described in, for example, Huang, X., et al., *Journal of Advanced Research* 1(1):13-28 (2010).

Nanoparticles can be functionalized as desired to link the nanoparticle to a protein. Exemplary functionalization of nanoparticles is described in the aforementioned U.S. Patent Publication No. 2012/0282632. As an example, a nanoparticle can be functionalized to present one or more carboxylic acid moieties, which in turn can be used to link one or more linker to a protein. The conjugate components (e.g., protein and nanoparticle) can be linked covalently or non-covalently. An example of a non-covalent linkage is a biotin-streptavidin affinity linkage in which one member of the conjugate is biotinylated and the other member of the conjugate is linked to streptavidin. Other examples of linkage options include, but are not limited to, direct coupling of nanoparticles to protein amines; modification of nanoparticles with maleimide and subsequent linkage to a protein having an exposed thiol group (generated, for example, by treating the protein with mercaptoethylamine or 2-iminothiolane (Traut's reagent)); modification of nanoparticles with hydrazine and linkage to a protein with oxidized glycan (aldehyde); or use of click chemistry (e.g., modification of nanoparticles with strained alkyne and linkage to an protein modified with azide).

Any type of conjugation methods can be used for conjugating a protein to a nanoparticle. Generally, to generate a desired yield of conjugate, an excess of protein is provided in the conjugation reaction. This can result in a significant amount of free (unconjugated) protein following the conjugation reaction. In some embodiments, there is also an amount of free unconjugated nanoparticles in the reaction mixture. The methods described herein are useful for purifying the conjugates from the free unconjugated members of the conjugation reaction. In some embodiments, a reagent is applied that will react with remaining reactive groups and prevent further reaction. As an example, conjugation between a maleimide-functionalized nanoparticle and a thiolated or reduced protein will be stopped or quenched with an alkylating reagent including, but not limited to, N-ethylmaleimide. The reaction between an NHS-appended nanoparticle and a protein will be stopped or quenched with an amine including, but not limited to, ethanolamine.

Once a conjugation has been performed, the resulting conjugation mixture (e.g., nanoparticle/protein conjugate, unreacted free protein and optionally free nanoparticle) is adjusted to establish an appropriate pH, conductivity, and/or concentration of salt. Adjustments can be made to the conjugation mixture (i.e., the sample to be purified) by, for example, exchanging a conjugation buffer with a chromatography resin equilibration buffer. Exemplary buffering compounds include, but are not limited to, phosphate, HEPES, IVIES, and Tris. In some embodiments, the equilibration buffer comprises HEPES in an amount ranging from about 10 mM to about 30 mM (e.g., 10 mM, 20 mM or 30 mM). In some embodiments, the equilibration buffer comprises phosphate ($PO_4^{3-}$) in an amount ranging from about 5 mM to about 50 mM (e.g., 5 mM, 10 mM, 25 mM). In certain embodiments, the equilibration buffer pH ranges from about 5 to about 8 (e.g., about 6, about 7, or about 8). In some embodiments, the equilibration buffer comprises at least 10 to 100 mM $Na^+$ or $K^+$ (e.g., between 10-150 mM, 20-200 mM, or 100-300 mM). In certain embodiments, the equilibration buffer is 20 mM HEPES-KOH pH 7.3. In some embodiments, the equilibration buffer is phosphate buffered saline (PBS=10 mM sodium phosphate, 150 mM sodium chloride pH 7.8).

One or more surfactants can also be included in the mixture. A sufficient amount of the surfactant can be included to prevent aggregation and precipitation of the conjugates in the mixture, especially upon introduction of a high ionic strength buffer, which might otherwise result in aggregation or precipitation of the conjugates. In some embodiments, the surfactant is a nonionic polyalkylene glycol surfactant such as polyethylene glycol. In some embodiments, the surfactant is a polyoxypropylene-containing surfactant such as a poloxamer surfactant. Poloxamer surfactants are characterized by a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist that have slightly different properties. Poloxamer copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic and Synperonic poloxamer tradenames, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobic chain; and the last digit×10 gives the percentage polyoxyethylene content (e.g., F-68 indicates a polyoxypropylene molecular mass of 1,800 g/mol and a 80% polyoxyethylene content). An exemplary poloxamer surfactant includes, but is not limited to, Pluronic F-68. The concentration of the surfactant used can be determined empirically (i.e., titrated such that precipitation of the conjugates does not occur). In some embodiments, the concentration of surfactant is 0.02%-1%, e.g., 0.05-0.2%, e.g., 0.1%.

Prior to contacting the sample (e.g., the conjugate mixture) to the agarose-filled ceramic apatite bead, the beads can be equilibrated to establish an appropriate pH, conductivity, and/or concentration of salts.

After contacting the sample to the agarose-filled ceramic apatite beads, the target molecule (e.g., the protein-nanoparticle conjugate) is excluded from the agarose-filled pores of the beads and is collected in the flow-through from the beads. The contaminants, e.g., free antibody (and optionally unconjugated nanoparticles) are captured by the ceramic apatite groups in the pores of the beads.

The output from the beads can be monitored for the presence of the target molecule or other components of the sample, as desired, to determine fractions that contain the target molecule and that are free, or at least have a reduced amount, of contaminant compared to the original sample. In some embodiments, at least 90%, 95%, 99% of the contaminant in the sample is removed in the resulting purified target molecule fractions. An exemplary method for measuring output includes monitoring a characteristic absorbance wavelength for the target molecule. The term "fraction" is used to refer to a portion of the output of chromatography and is not intended to limit how the output is collected or whether the output is collected in parts or continuously.

EXAMPLES

Example 1—Selectivity and Binding Capacity of Agarose-Filled Ceramic Apatite (CHT)

The purpose of this example was to determine if selectivity and binding capacity of CHT are changed by filling the pores of the CHT with agarose.

Preparation of 1% Agarose-Filled CHT

A 1% agarose solution was made by dissolving 0.5 g of agarose (Hispanagar D5 High Gel Strength) in 50 ml water at 100° C. 10 ml of dry CHT (Bio-Rad Type II) and 15 ml hot agarose solution were mixed in a 100 ml flask, and then a vacuum was applied to the mixture for a few seconds to remove air trapped inside the CHT beads. The mixture was then transferred to a chromatography column and either air pressure or vacuum suction was applied for 15 minutes to remove excess agarose solution from the packed bed. The CHT containing agarose solution was then transferred to a beaker and stored at 4° C. to form an insoluble gel inside the pores of the ceramic apatite.

To determine the effect of inclusion of agarose in the CHT beads, the ability of the CHT was tested with and without agarose on a sample containing myoglobin and cytochrome C. The conditions tested were as follows:

Column: 0.7×5.6 cm
Flow rate: 2 ml/min (300 cm/hr)
Buffer A: 10 mM sodium phosphate pH 6.8
Buffer B: 400 mM sodium phosphate pH 6.8
Gradient: 0-100% B 40 ml
Sample: myoglobin and cytochrome C (both from Sigma-Aldrich)

The results of protein separation are shown in the overlay (showing both runs) chromatogram of FIG. 1. No significant difference was observed for the selectivity (e.g., retention time of proteins) of the resin with or without agarose, indicating that the agarose was likely embedded within the CHT, and did not interfere with the surface of the pores of the CHT.

The dynamic binding capacity of the agarose-filled CHT resin for human IgG was also tested and compared to untreated CHT under the following conditions:

Column: 0.7×5.6 cm
Flow rate: 2 ml/min (1 min residence time)
1 ml/min (2 min residence time)
Loading buffer: 10 mM sodium phosphate pH 6.8
Elution buffer: 400 mM sodium phosphate pH 6.8
Sample: 5 mg/ml human IgG in 10 mM sodium phosphate pH 6.8

The dynamic binding capacity results are summarized in Table 1 below. As shown in Table 1, the human IgG binding capacity of agarose filled-CHT was only slightly reduced with a 17% decrease at 2 ml/min, and a decrease of 14% at 1 ml/min.

TABLE 1

|  | Human IgG Binding Capacity (10% breakthrough) 2 ml/min | Human IgG Binding Capacity (10% breakthrough) 1 ml/min |
| --- | --- | --- |
| CHT | 38.6 mg/ml | 45.9 mg/ml |
| Agarose filled-CHT | 31.8 mg/ml | 39.3 mg/ml |

This example illustrates that the CHT selectivity and binding capacity are not significantly affected by filling the pores of the CHT with agarose.

Example 2: Comparison of Chromatographic Properties of Agarose-Filled CHT to Commercially Available Resins The purpose of this example was to determine if the chromatographic properties of the CHT are changed by filling the pores of the CHT with agarose. The chromatographic properties of the agarose-filled CHT were also compared to Capto Core 700 (GE Healthcare). IgG-pdot conjugate (which has a molecular weight greater than 500 kDa) was applied to each resin to determine if the conjugate bound to each resin or was excluded in the void volume. Bovine hemoglobin was also applied to 4% agarose-filled CHT to determine if the agarose-filled pores allowed a molecule having a molecular weight of about 64 kDa to enter the pores of and to be captured by the agarose-filled CHT.

Preparation of 4% Agarose-Filled CHT

A 4% solution of agarose was made by dissolving 2 g of agarose (Hispanagar D5 High Gel Strength) in 50 ml water at 100° C. 5 grams of dry CHT (Bio-Rad Type II) and 20 grams hot agarose solution were mixed in a 100 ml flask, and then a vacuum was applied to the mixture for a few seconds to remove air trapped inside the CHT beads. The mixture was stirred while adding 40 ml hot (approximately 70° C.) Isopar H (ExxonMobil Chemical) followed by 0.5 ml Span 80 (Sigma-Aldrich). Isopar H and Span 80 were added to the solution to create a stable suspension and to prevent the pore-filled CHT particles from aggregating, respectively. The mixture was then cooled in an ice bath while stirring to form an insoluble gel inside the pores of the ceramic apatite. Finally, the agarose filled CHT was washed with water and was sized with a sieve to yield beads having a diameter ranging from 25 μm-75 μm. The presence of agarose in the pores of the CHT was verified by the ability of the agarose filled CHT to chromatographically exclude IgG-pdots from the pores (see Chromatographic Property Comparison below).

Chromatographic Property Comparison

Five disposable columns (Bio-Rad Micro Bio-Spin™ Chromatography Columns; used in gravity mode) were packed with 0.75 mls of resin as described in Table 2. The columns were equilibrated with 3-4 ml PBS buffer which had 10 mM sodium phosphate pH 7.8, 150 mM sodium chloride, 0.1% pluronic F68 (Thermo Fisher), and 0.1% PEG 3350 (Sigma-Aldrich). A 10 μl sample of purified goat anti-rabbit IgG-pdot conjugate or 2 mg/ml bovine hemoglobin (Sigma-Adrich) in PBS buffer was applied to each column. The conjugate was prepared by modifying pdots with maleimide and then linking the pdots to the IgG through thiol groups (generated by treating the antibody with Traut's reagent). The pdots absorb at 470 nanometers and have a reddish-brown color; thus, the conjugate had a reddish-brown color. A solution of bovine hemoglobin also has a reddish-brown color.

After the samples were applied, the columns were washed with 500 μl PBS buffer. Binding of the samples to the resins was determined visually, i.e., a red color at the top of the column or dispersed throughout the resin indicated that the sample bound to the resin. If the red color was in the flow-through solution, then the sample did not bind to the resin (e.g., the sample is unbound). The results are summarized in Table 2.

TABLE 2

|  | Column 1 | Column 2 | Column 3 | Column 4 | Column 5 |
| --- | --- | --- | --- | --- | --- |
| Resin | Capto ™ Core 700 (GE Healthcare) | CHT (untreated) | 4% Agarose-filled CHT | 4% Agarose-filled CHT | 1% Agarose-filled CHT (from Example 1) |
| Sample | IgG-pdot conjugate | IgG-pdot conjugate | hemoglobin | IgG-pdot conjugate | IgG-pdot conjugate |
| Result | bound | bound | bound | unbound | bound |

The results in Table 2 indicate that the IgG-pdot conjugate binds to Capto™ Core 700, CHT, and 1% agarose-filled CHT but not to the 4% agarose-filled CHT. Hemoglobin also binds to the 4% agarose-CHT. Thus, filling the pores and coating the surface of the CHT with 4% agarose blocks the large conjugate from binding to the CHT while allowing smaller molecules (e.g., hemoglobin) to enter the pores and to bind to the surface inside the pores of the CHT. Without being bound to a particular theory, it is believed that 1% agarose was not a sufficiently high enough agarose concentration to completely coat the outer surface of the CHT beads to prevent binding of the conjugate to the outer surface of the CHT beads.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A ceramic apatite bead comprising an insoluble porous polymer, the ceramic apatite bead comprising an insoluble porous polymer made by a method comprising:
   incubating ceramic apatite in a heated polymer solution;

filtering the heated polymer solution with positive or negative pressure to remove excess polymer from the ceramic apatite beads; and cooling the heated polymer solution having ceramic apatite to between about 4° C. to about 30° C. to form an insoluble porous polymer gel within the pores of the ceramic apatite beads.

2. The ceramic apatite bead of claim 1, wherein the polymer is agarose.

3. The ceramic apatite bead of claim 2, wherein the agarose is not cross-linked.

4. The ceramic apatite bead of claim 2, wherein the agarose has a concentration ranging from about 1% to about 8%.

5. The ceramic apatite bead of claim 1, wherein the ceramic apatite is ceramic hydroxyapatite.

6. A chromatography column comprising a plurality of ceramic apatite beads according claim 1.

7. The ceramic apatite bead of claim 1, wherein the filtering comprises negative pressure, wherein the negative pressure is from a vacuum.

8. The ceramic apatite bead of claim 1, wherein the filtering comprises positive pressure.

9. A method of performing chromatography, the method comprising contacting a sample comprising a target molecule to a plurality of ceramic apatite beads according to claim 1 under conditions such that the target is not captured by the ceramic apatite beads; and collecting the target molecule from the ceramic apatite beads.

10. The method of claim 9, wherein the sample comprises a contaminant that is captured by the ceramic apatite beads.

11. The method of claim 9, wherein the target molecule is a protein-nanoparticle conjugate and the contaminant is free protein.

12. The method of claim 9, wherein the sample comprises a protein-nanoparticle conjugate, free protein, and a buffer.

13. The method of claim 12, wherein the sample further comprises a surfactant.

14. The method of claim 13, wherein the surfactant is polyalkylene glycol.

15. The method of claim 9, wherein the collecting step comprises collecting one or more fractions enriched for the target molecule from the ceramic apatite beads.

16. The method of claim 9, wherein the collecting step comprises applying centrifugal force or a vacuum to the ceramic apatite beads and collecting one or more fractions enriched for the target molecule from the ceramic apatite beads.

17. The method of claim 11, wherein the protein is an IgG antibody.

18. The method of claim 11, wherein the protein-nanoparticle conjugate is a protein-polymer dot conjugate.

19. The method of claim 14, wherein the surfactant is a poloxomer having a polyoxypropylene molecular mass of 1,800 g/mol and a 80% polyoxyethylene content.

20. The method of claim 11, wherein the sample further comprises free nanoparticles and the ceramic apatite beads separate the free nanoparticles from the protein-nanoparticle conjugate.

* * * * *